United States Patent [19]

Chung et al.

[11] Patent Number: 5,693,545

[45] Date of Patent: Dec. 2, 1997

[54] METHOD FOR FORMING A SEMICONDUCTOR SENSOR FET DEVICE

[75] Inventors: Young Sir Chung, Gilbert; Keenan L. Evans, Tempe; Henry G. Hughes, Scottsdale; Ronald J. Gutteridge, Paradise Valley, all of Ariz.

[73] Assignee: Motorola, Inc., Schaumberg, Ill.

[21] Appl. No.: 608,160

[22] Filed: Feb. 28, 1996

[51] Int. Cl.[6] ................................................ H01L 21/77
[52] U.S. Cl. .......................... 437/40 R; 437/2; 437/228; 437/921
[58] Field of Search ........................ 437/40 R, 2, 901, 437/921; 204/416, 418, 422, 424; 148/DIG. 159

[56] References Cited

U.S. PATENT DOCUMENTS

| | | | |
|---|---|---|---|
| 4,020,830 | 5/1977 | Johnson et al. | 204/416 |
| 4,411,741 | 10/1983 | Janata | 437/170 |
| 5,004,700 | 4/1991 | Webb et al. | 437/228 SEN |
| 5,035,791 | 7/1991 | Battlotti et al. | 204/416 |
| 5,350,701 | 9/1994 | Jaffrezic-Renault et al. | 204/418 |
| 5,417,821 | 5/1995 | Pyke | 204/416 |
| 5,576,563 | 11/1996 | Chung | 257/253 |

*Primary Examiner*—Michael Trinh
*Attorney, Agent, or Firm*—Robert F. Hightower

[57] ABSTRACT

A method for forming a semiconductor sensor FET device (2) comprises the steps of forming spaced-apart doped source (6) and drain (8) regions in a semiconductor substrate (4) with electrically conductive paths (16, 18) to each region. The region between the source (6) and drain (8) regions defines a gate region (12). An insulating layer (14, 15) is formed on the substrate (4) and source and drain regions (8), and a cantilever gate structure is formed using a sacrificial layer (60), such that a gate electrode (26) is supported on a cantilever support (28) and a cavity (22) separates the gate electrode (26) from the gate region (12). A conductive layer (34) is formed overlying the gate electrode (26) to provide a heater for the gate electrode (26). The chemical species collect in the cavity (22) and react with the surface (27) of the gate electrode (26).

15 Claims, 4 Drawing Sheets

METHOD FOR FORMING A SEMICONDUCTOR SENSOR FET DEVICE

FIELD OF THE INVENTION

This invention relates to a method for forming semiconductor sensor Field Effect Transistor (FET) devices and semiconductor sensor FET devices. More particularly, this invention relates to a method for forming semiconductor chemical sensor FET devices.

BACKGROUND OF THE INVENTION

A chemical sensor is a device which monitors the concentration of a given chemical species in a liquid or a gas. Chemical sensors are used, for example, to detect unsafe levels of poisonous or explosive gases in the work and home environments.

Typically chemical sensors comprise a sensitive layer, which is sensitive to particular chemical species which are to be detected by the sensor. The reaction of the sensitive layer with the chemical species to be detected results in a change in the physical properties of the sensitive layer, e.g. resistivity or surface potential. As the reaction of the sensitive layer is governed by thermodynamic relations, temperature plays an important role in optimizing the output of the sensor device, e.g. sensitivity and selectivity.

Known metal oxide semiconductor devices, such as the sensor described in French patent application no. 9507903, are produced by complex processes that are incompatible with, for example, CMOS processes. The sensing materials on these types of devices need to be operated at high temperatures, around 450° C., thus resulting in relatively high power consumption. The operating mechanism for these previously known sensors is based on a change in resistivity of the sensing element due to reduction and oxidation reaction of a gaseous species. This modulates the electric charge concentration in the material and the grain boundaries and results in a change in resistivity. Such reduction and oxidation based reaction mechanisms used in the previously known sensors are inherently slow relative to surface reaction mechanisms.

Field Effect Transistors (FETs) have been previously used in some cases as chemical sensors for measuring the concentration of a chemical in a fluid. U.S. Pat. No. 4,411,741 describes an example of such a FET sensor which uses a gate electrode that is suspended over the channel region so as to provide a gap in which a fluid may enter and contact an exposed surface of the gate electrode. A chemical in the fluid, to which the gate electrode is particularly sensitive, is adsorbed onto the exposed surface and changes the surface potential of the gate electrode. The drain current of the transistor changes in response to this surface potential change.

It has been found that the surface chemical reactions of such a FET chemical sensor are very sensitive to temperature. In order to regulate the temperature of the gate electrode so as to optimise the output of the sensor, an external heater is used to heat the entire sensor assembly. An external heater requires significant power consumption during operation and is inconvenient to provide in a final, fully manufactured chemical sensor assembly and increases the manufacturing cost thereof.

U.S. patent application Ser. No. 8/427,389, filed by the assignee of the present application on 14th Apr. 1995, now U.S. Pat. No. 5,576,563, describes a sensor device comprising a chemically sensitive FET having an embedded heater to control the temperature of a chemically sensitive gate electrode surface. Having an integrated heater provides direct temperature control of the gate electrode without the disadvantages of the external heater.

There is a need to provide a method of forming such a chemically sensitive FET having stable and uniform chemical detection characteristics and an integrated heater, which method is also compatible with processes such as CMOS processes.

SUMMARY OF THE INVENTION

In accordance with a first aspect of the present invention there is provided a method for forming a semiconductor sensor FET device comprising the steps of:

providing a semiconductor substrate;

forming spaced-apart doped source and drain regions in the semiconductor substrate at a surface of the semiconductor substrate, the portion of semiconductor substrate between the source and drain regions defining a gate region;

forming a first insulating layer on the surface of the substrate;

patterning and etching first and second openings through the first insulating layer to the source and drain regions respectively;

filling the first and second openings with conductive material to provide electrically conductive paths to the source and drain regions;

forming a second insulating layer on the first insulating layer and electrically conductive paths;

forming a sacrificial layer on a portion of the second insulating layer such that the sacrificial layer extends over the source, gate and drain regions;

forming a sensing element on a portion of the sacrificial layer adjacent the gate region, the sensing element forming the gate electrode;

forming a third insulating layer over the sensing element, a substantial part of the sacrificial layer and part of the second insulating layer;

patterning and etching an opening through the third insulating layer to the sensing element;

filling the opening with conductive material to provide an electrically conductive path to the sensing element;

forming a conductive layer overlying the sensing element, the conductive layer providing a heater for the sensing element; and removing the sacrificial layer so as to provide a cavity between the sensing element and second insulating layer.

Thus, the method in accordance with the invention provides stable, reproducible sensor FET devices that are useful for detecting specific components in liquid or gaseous fluids.

BRIEF DESCRIPTION OF THE DRAWINGS

A semiconductor sensor FET device in accordance with the invention and a method for forming a semiconductor sensor FET device in accordance with the invention will now be described, by way of example only, with reference to the accompanying drawings in which.

DETAILED DESCRIPTION

Figure 1:
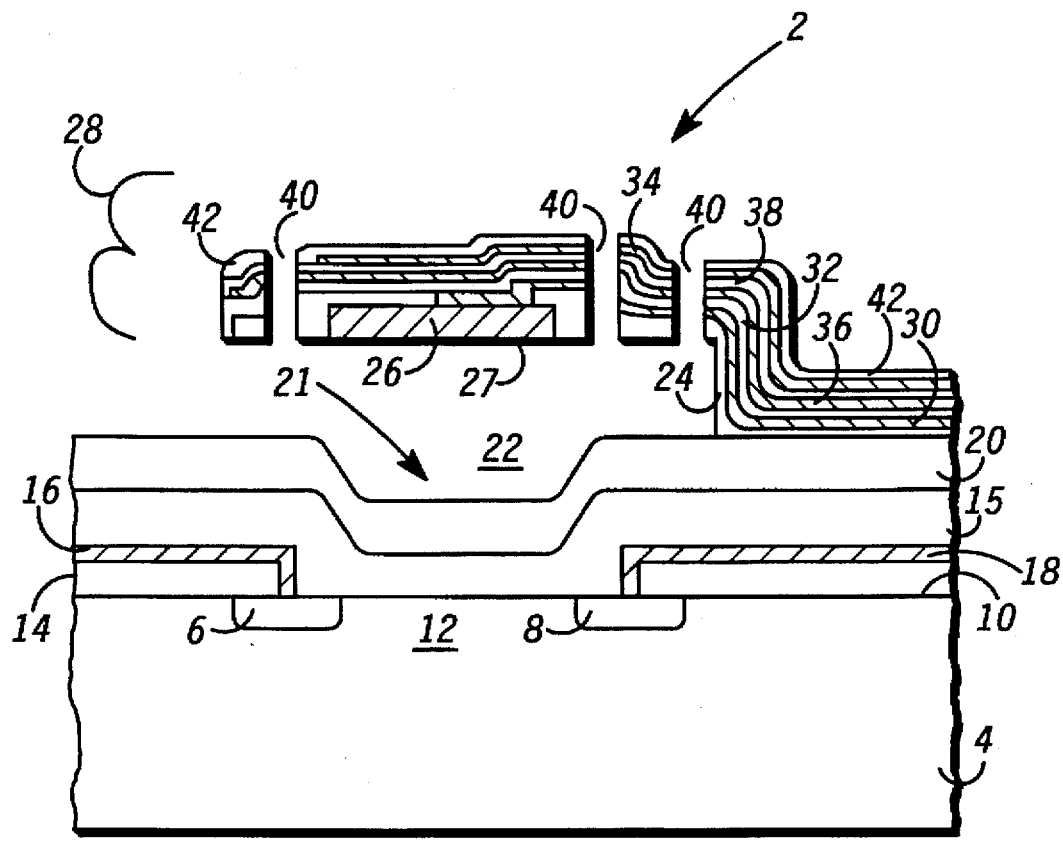
FIG. 1 shows a simplified schematic cross-sectional view of a semiconductor sensor FET device in accordance with the present invention.

Referring firstly to FIG. 1, a semiconductor sensor FET device 2 in accordance with a preferred embodiment of the invention comprises a semiconductor substrate 4 having spaced-apart doped source 6 and drain 8 regions formed therein, the regions 6 and 8 extending from a surface 10 of the semiconductor substrate 4. The portion of the semiconductor substrate 4 between the source 6 and drain 8 regions defines a gate region 12 or channel.

A first insulating layer 14 is formed on the surface 10 of the substrate 4. First 16 and second 18 contact leads provide electrically conductive paths through the first insulating layer 14 to the source 6 and drain 8 regions, respectively. The first and second contact leads 16 and 18 are comprised of electrically conductive materials such as aluminium, or polysilicon and conduct current away from the source 6 and drain 8 regions.

A second insulating layer 15 is formed over the first insulating layer 14 and first and second contact leads 16 and 18.

In the preferred embodiment an additional insulating layer 20 is formed over the second insulating layer 15. This additional insulating layer 20 acts as a passivation layer. The first 14 and second 15 insulating layers and passivation layer 20 may each comprise a silicon dioxide, silicon nitride or a tantalum oxide layer or any combination thereof. When both the first and second insulating layers are formed from the same material, they appear as one layer. Preferably, the first insulating layer 14 comprises a silicon dioxide layer, the second insulating layer 15 also comprises a silicon dioxide layer and the passivation layer 20 comprises a silicon nitride layer. The first 14 and second 15 insulating layers and passivation layer 20 between the source 6 and drain 8 regions are known as the gate insulators.

A third insulating layer 24 having a sensing element 26 formed therein adjacent the gate region 12 is formed over the passivation layer 20 to form a cantilever support 28, wherein a cavity 22 is formed between the passivation layer 20 and the third insulating layer 24, including the area between the sensing element 26 and gate region 12. The cavity has a depth in the range of 0.01 microns to 20 microns. The sensing element 26 forms the gate electrode and has a surface 27 exposed to the cavity 22.

Chemical species collect in the cavity 22 and depending on the material from which the sensing element 26 is formed and the temperature of the sensing element 26, specific chemical species react with the surface 27 of the sensing element 26. The sensing element 26 may be formed from a gold layer, or a gold-palladium alloy layer for sensing hydride gases. For a carbon monoxide sensor device, the sensing element 26 may comprise a tin oxide layer. The type of sensitive material which is used to form the sensing element 26 may vary from metals to doped/compound materials and depends on the applications and the type of chemicals the sensor FET device 2 is to detect.

In the preferred embodiment, the second insulating layer 15 is etched so as to provide a well 21 in the second insulating layer 15 and passivation layer 20 in the vicinity of the gate region 12.

A third contact lead 30 provides an electrically conductive path to the sensing element through the third insulating layer 24.

A fourth insulating layer 32 is formed on the third insulating layer 24 and third contact lead 30, and a shield layer 36 is formed over the fourth insulating layer 32. A fifth insulating layer 38 is formed over the shield layer 36 and a conductive layer 34 is formed over at least a portion of the fifth insulating layer 38, which conductive layer forms a heater for the sensing element 26. An optional passivation layer 42 is then formed over the conductive layer 84.

The third insulating layer 24, sensing element 26, contact lead 30, fourth insulating layer 32, shield layer 36, fifth insulating layer 38, conductive layer 34 and passivation layer 42 form a cantilever structure supported by the cantilever support 28.

Optionally, an additional metal layer (not shown) such as chromium, titanium or vanadium can be deposited on the third insulating layer 24 before the third contact lead 30 is formed to enhance the adhesion between the sensing element 26 and third insulating layer 24. A further barrier layer (not shown), such as a nickel layer, may also be formed on the additional metal layer.

The shield layer 36 and fifth insulating layer 38 may be omitted, in which case the conductive layer 34 is formed over the fourth insulating layer 32. However, it is preferred that the shield layer 36 is used between the conductive layer 34 and the second insulating layer 24 to protect the gate electrode or sensing element 26 from electrical interference from the heater and various other external electrical noise sources.

In the preferred embodiment, the semiconductor sensor FET device 2 further comprises at least one hole 40, extending through the passivation layer 42, and the other layers to the cavity 22. The at least one hole 40 provides vertical accessibility of the chemical species onto the surface 27 of the sensing element 26 (gate electrode) as well as lateral accessibility.

The third 24, fourth 32 and fifth 38 insulating layers and passivation layer 42 may each comprise a silicon dioxide, silicon nitride or a tantalum oxide layer or any combination thereof. Preferably, the shield layer comprises doped polysilicon, aluminium, or other conductive material and the conductive layer 34 is formed from any materials which can provide heat as a function of electrical power, such as polysilicon, metals for example platinum, nickel/chromium alloys and heavily doped silicon.

A method for forming a semiconductor sensor FET device 2 in accordance with the preferred embodiment of the present invention will now be described with reference to FIGS. 1-8.

In the following description, the different semiconductor layers and regions are described as having a particular type of conductivity. This is by way of illustration only and it is not intended to limit the invention to the specific conductivity type described herein.

Figure 2:
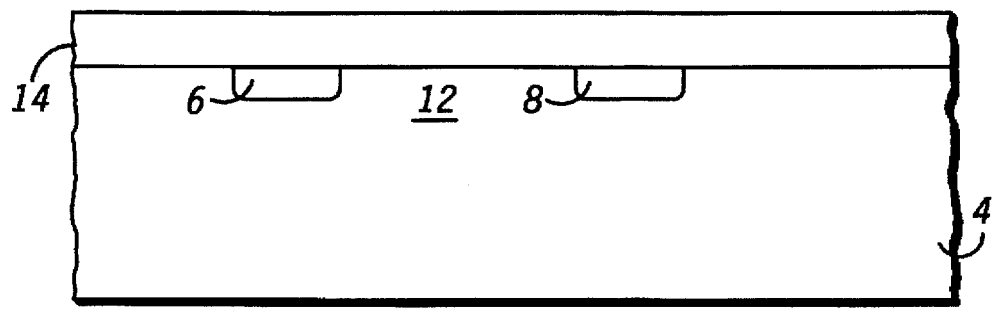
FIGS. 2–8 show simplified schematic cross-sectional views of the semiconductor sensor FET device of FIG. 1 during different stages of fabrication.

Firstly, a semiconductor substrate 4 is provided having a p-type conductivity. Using well known doping techniques, two spaced-apart doped regions 6 and 8 are formed on the semiconductor substrate 4 having n-type conductivity (FIG. 2). One of the doped regions 6 is the source region and the other doped region 8 is the drain region of a FET. A first insulating layer 14 is thermally grown or deposited over the substrate 4 and the source 6 and drain 8 regions.

Figure 3:
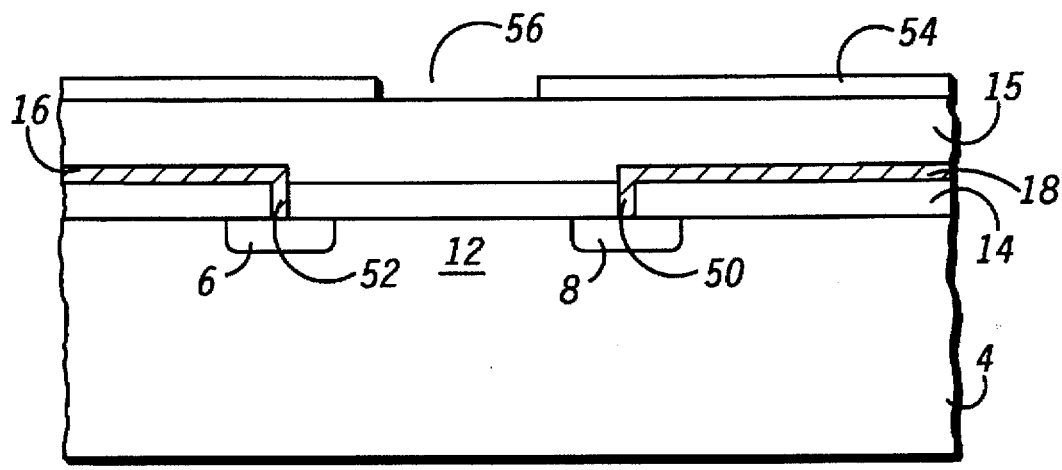

First 52 and second 50 openings 50 and 52 are patterned and etched through the first insulating layer 14 to the source 6 and drain 8 regions, respectively (FIG. 3). The first 52 and second 50 openings are then filled with an electrically conductive material, such as polysilicon, to form electrically conductive paths or first 16 and second 18 contact leads to the source 6 and drain 8 regions, respectively. A second insulating layer 15 is then thermally grown or deposited over the first and second contact leads 16 and 18 and the first insulating layer 14. In the preferred embodiment, the first 14 and second 15 insulating layers are formed from the same material, silicon dioxide and thus, appear as one layer.

In the preferred embodiment, a mask 54 is then formed on the second insulating layer 15 having an opening 56 adjacent the gate region 12. The second insulating layer 15 is then etched substantially to the first insulating layer 14 to form a well in the second insulating layer.

Figure 4:
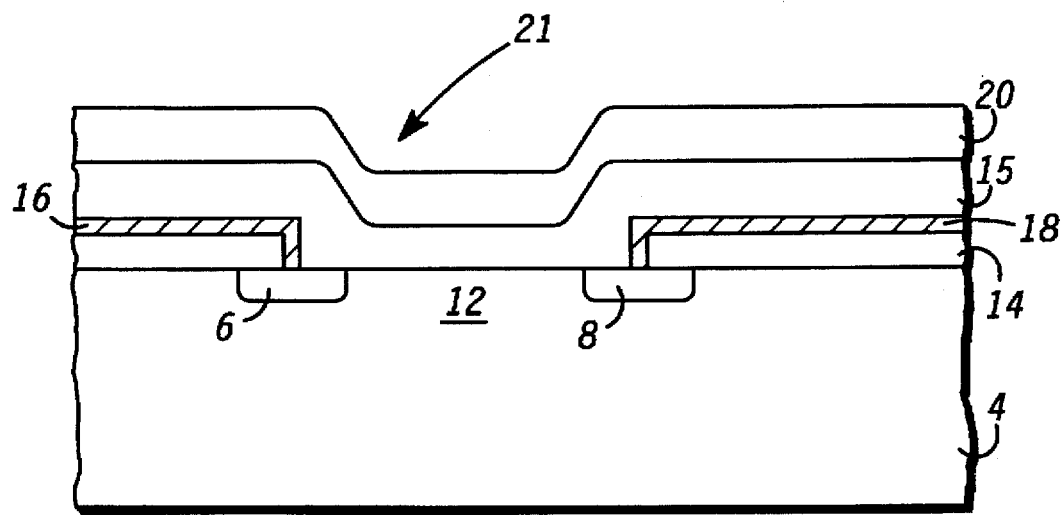

An optional passivation layer 20, formed from preferably silicon nitride, is deposited on the second insulating layer (FIG. 4). This passivation layer 20 protects the sensor FET device 2, and particularly the gate region 12, from the environment and from the sacrificial layer etching described below. This improves the stability of the sensor FET device 2. In the region where the second insulating layer 15 has been etched, a well 21 is formed.

Figure 5:
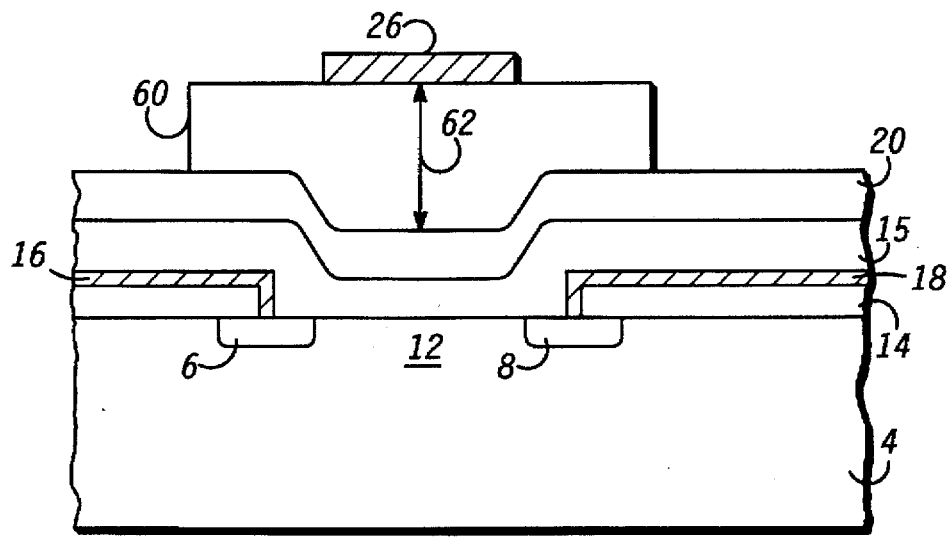

A sacrificial layer 60, such as phosposilicate glass (PSG), having a controlled thickness is then deposited onto the passivation layer 20 (FIG. 5). The sacrificial layer will be removed later to provide the cavity 22 which allows the chemical species access onto the surface 27 of the sensing element or gate electrode 26. For this reason, the thickness 62 of the sacrificial layer is closely controlled and is preferably between 0.01 to 20 microns. The thickness of the sacrificial layer 60 determines the depth of the cavity 22.

A sensing element 26 is formed on the sacrificial layer 60 adjacent the gate region 12. The sensing element 26 is formed by depositing a layer of sensitive material, such as gold, and then patterning and etching the layer to form the sensing element 26. The sensing element 26 forms the gate electrode.

Figure 6:
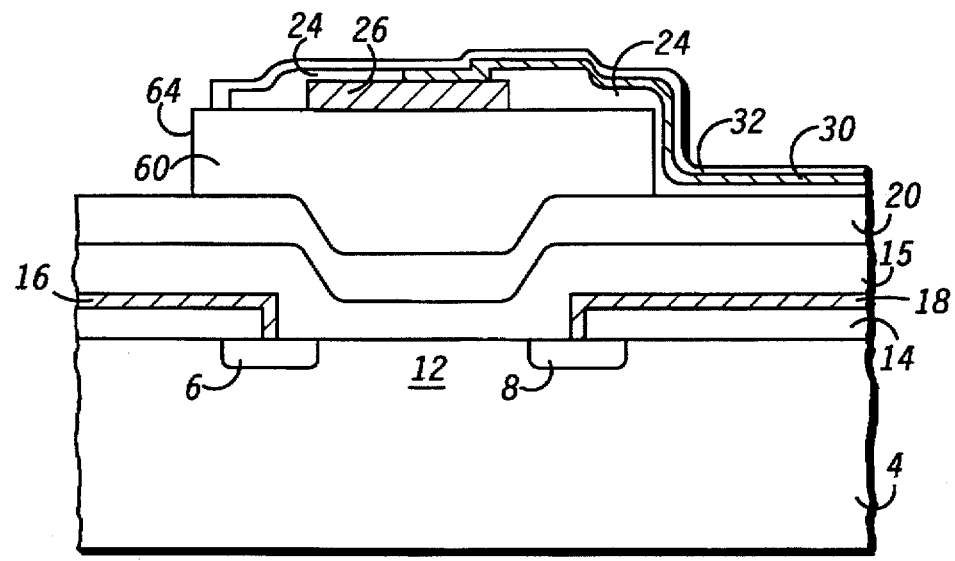

A third insulating layer 24 is deposited to cover the sensing element 26, a substantial part of the sacrificial layer 60 and part of the passivation layer 20 (FIG. 6). At least one side 64 of the sacrificial layer 60 is not covered by the third insulating layer 24. Preferably, the third insulating 15 layer 24 is formed from silicon nitride material. An opening is then etched in the third insulating layer 24 through to the sensing element or gate electrode 26. The opening is then filled with electrically conductive material, such as polysilicon, to form an electrically conductive path or third contact lead 30 to the sensing element or gate electrode 26. A fourth insulating layer 32, such as a silicon nitride layer, is deposited over the third insulating layer 24 and third contact lead 30.

Figure 7:
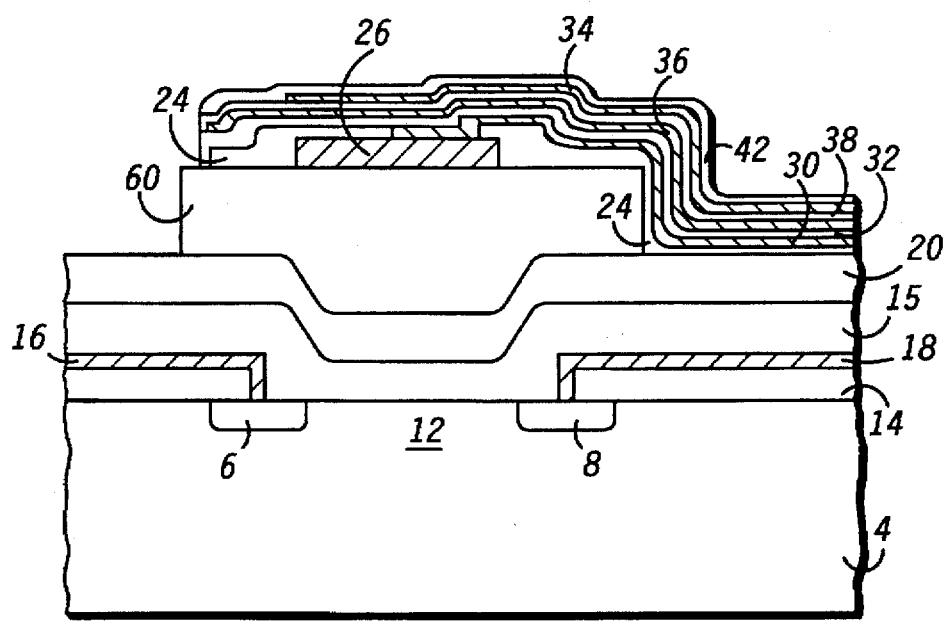

In the preferred embodiment, a shield layer 36 is then deposited over the fourth insulating layer 32 (FIG. 7). The shield layer 36 is preferably formed from polysilicon and protects the sensing element or gate electrode 26. A fifth insulating layer 38, such as a silicon nitride layer, is then deposited onto the shield layer 36. A conductive layer 34, formed from for example polysilicon material, is then formed on the fifth insulating layer 38. The conductive layer 34 forms a heater to heat the sensing element 26 of the sensor FET device 2. The fourth and fifth insulating layers provide electrical isolation from the shield 36 and conductive 34 layers.

Optionally, a passivation layer 42 may be deposited on the conductive layer 34 to protect the heater from the environment. The passivation layer preferably comprises a silicon nitride layer.

Figure 8:
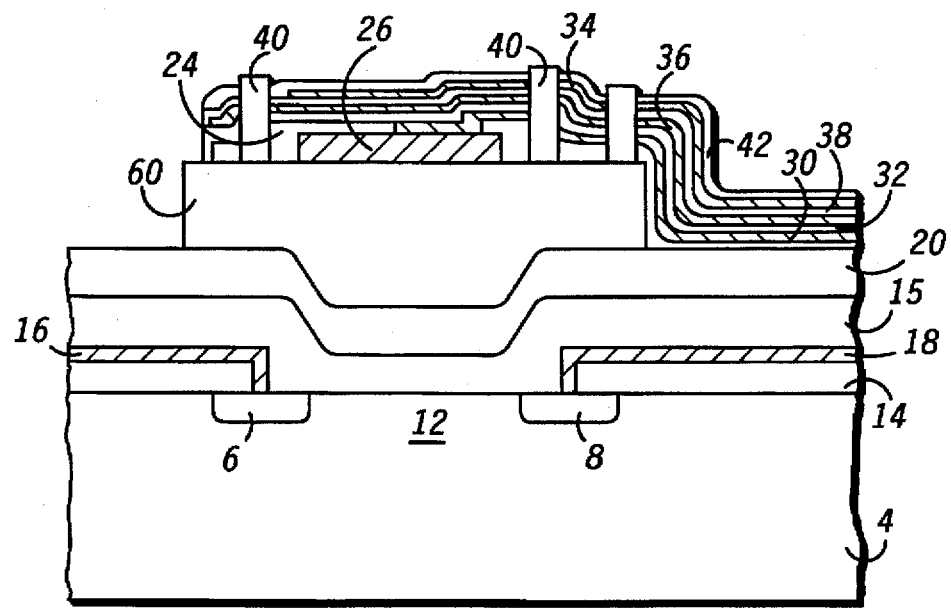

In the preferred embodiment, at least one hole 40 is formed through the passivation layer 42 to the sacrificial layer 60 (FIG. 8). The at least one hole can be made using various standard etching and milling techniques.

The sacrificial layer 60 is then removed to provide a cavity 22 between the cantilever support 28, formed by the third insulating layer 24, and the passivation layer 20. In the case when the sacrificial layer 60 is formed from PSG material, an etching solution, such as a hydrogen fluoride (HF) solution, can be used to etch the sacrificial layer 60.

The at least one hole 40 enhances the etching rate of the sacrificial layer 60 and also provides vertical accessibility of the chemical species onto the surface 27 of the sensing element or gate electrode 26.

The semiconductor sensor FET device in accordance with the invention operates as follows. Chemical species collect in the cavity 22. At certain temperatures, specific chemical species react with the surface 27 of the sensing element or gate electrode 26 (adsorption-desorption reaction), which reaction causes a change in potential at the gate electrode. The change in potential is a function of the concentration of the chemical species which react at the surface 27. Thus, by monitoring the current flowing in the drain and source conductive paths, the changes in gate electrode potential and hence the presence and concentration of particular chemical species can be detected.

The heater, formed by conductive layer 34, is directly incorporated into the sensor FET device and controls the kinetics of the adsorption-desorption reaction of the gate electrode as a function of temperature. This is critical for optimisation of sensor outputs, such as sensitivity and selectivity, for continuous operation, calibration and re-generation.

The present invention provides a semiconductor sensor FET device having a cantilevered gate structure. That is the gate electrode 26 is formed on a cantilever support 28 such that a cavity 22 separates the gate electrode 26 from the gate region 12. An advantage of such a structure is that it ensures good lateral accessibility of the chemical species to the surface of the gate electrode which ensures good exchange rates of the chemical species inside the cavity. Having at least one hole further improves accessibility and hence further improves the exchange rate.

A further advantage of the present invention is that the semiconductor sensor FET device in accordance with the present invention can be fabricated using well known conventional CMOS semiconductor processes and surface micro-machining processes, with no limitations on the type of materials which can be used for the sensing element or gate electrode. This means that the present invention can be fabricated without the need for special processes to be developed and hence cost effectively.

The size of the cavity can be precisely controlled using surface micromachining with a sacrificial layer. This ensures good reproducibility.

Since the present invention is compatible with CMOS processing, it is possible to integrate a circuit into the chemical sensor chip, providing a complete sensor system with signal processing and output circuitry onto a single chip. This compatibility thus provides a means to miniaturize the overall circuitry required to effectively utilize the chemical sensor FET device in a complete system. Volume production can be easily achieved using CMOS processes, since a single wafer contains thousands of devices. A significant reduction of the power consumption for controlling temperature is possible because only the gate electrode membrane structure is heated. Also, this local membrane heating results in substantially less temperature degradation effect on the MOSFET portion of the device and consequently enhances the life time of the device.

We claim:

1. A method for forming a semiconductor sensor FET device comprising the steps of:

providing a semiconductor substrate;

forming spaced-apart doped source and drain regions in the semiconductor substrate at a surface of the semiconductor substrate, the portion of semiconductor substrate between the source and drain regions defining a gate region;

forming a first insulating layer on the surface of the semiconductor substrate;

patterning and etching first and second openings through the first insulating layer to the source and drain regions respectively;

filling the first and second openings with conductive material to provide electrically conductive paths to the source and drain regions;

forming a second insulating layer on the first insulating layer and electrically conductive paths;

forming a sacrificial layer on a portion of the second insulating layer such that the sacrificial layer extends over the source, gate and drain regions;

forming a sensing element on a portion of the sacrificial layer adjacent the gate region, the sensing element forming the gate electrode;

forming a third insulating layer over the sensing element, a substantial part of the sacrificial layer and part of the second insulating layer;

patterning and etching an opening through the third insulating layer to the sensing element;

filling the opening with conductive material to provide an electrically conductive path to the sensing element;

forming a conductive layer overlying the sensing element, the conductive layer providing a heater for the sensing element; and removing the sacrificial layer so as to provide a cavity between the sensing element and second insulating layer.

2. A method for forming a semiconductor sensor FET device according to claim 1 further comprising, before the step of forming the sacrificial layer, the step of forming a passivation layer on the second insulating layer and wherein the step of forming the sacrificial layer comprises forming the sacrificial layer on the passivation layer.

3. A method for forming a semiconductor sensor FET device according to claim 2 further comprising, before the step of forming a passivation layer on the second insulating layer, the step of patterning and etching the second insulating layer to form a well in the second insulating layer adjacent the gate region.

4. A method for forming a semiconductor sensor FET device according to claim 2 wherein the first and second insulating layers and the passivation layer are each formed from any one of the following materials: silicon nitride, silicon dioxide, and tantalum oxide.

5. A method for forming a semiconductor sensor FET device according to claim 1 further comprising, before the step of forming the conductive layer, the step of forming a fourth insulating layer over the third insulating layer and the electrically conductive path to the sensing element, wherein the conductive layer is formed over a portion of the fourth insulating layer.

6. A method for forming a semiconductor sensor FET device according to claim 5 further comprising, before the step of forming the conductive layer, the steps of:

forming a shield layer on the fourth insulating layer; and forming a fifth insulating layer on the shield layer, and wherein the step of forming the conductive layer comprises forming the conductive layer on the fifth insulating layer.

7. A method for forming a semiconductor sensor FET device according to claim 1 further comprising, after the step of forming the conductive layer, the step of forming at least one hole through the conductive layer to the sacrificial layer.

8. A method for forming a semiconductor sensor FET device according to claim 1 further comprising the step of forming a passivation layer on the conductive layer.

9. A method for forming a semiconductor sensor FET device according to claim 1 further comprising the step of forming at least one additional metal layer on the third insulating layer.

10. A method for forming a semiconductor sensor FET device according to claim 1 wherein the step of forming a sacrificial layer comprises forming a sacrificial layer having a thickness in the range of 0.01 microns to 20 microns.

11. A method for forming a semiconductor sensor FET device according to claim 1 wherein the sensing element is formed from any one of the following materials: gold, gold-palladium alloy and tin oxide.

12. A method for forming a semiconductor sensor FET device according to claim 1 wherein the sacrificial layer is formed from phosposilicate glass.

13. A method for forming a semiconductor sensor FET device according to claim 12 wherein the removing step comprises the step of etching the sacrificial layer with a hydrogen fluoride solution.

14. A method for forming a semiconductor sensor FET device comprising the steps of:

providing a semiconductor substrate;

forming spaced-apart doped source and drain regions in the semiconductor substrate at a surface of the semiconductor substrate, the portion of semiconductor substrate between the source and drain regions defining a gate region;

forming a first insulating layer on the surface of the substrate;

patterning and etching first and second openings through the first insulating layer to the source and drain regions respectively;

filling the first and second openings with conductive material to provide electrically conductive paths to the source and drain regions;

forming a second insulating layer on the first insulating layer and electrically conductive paths;

forming a passivation layer on the second insulating layer;

forming a sacrificial layer on a portion of the passivation layer such that the sacrificial layer extends over the source, gate and drain regions;

forming a sensing element on a portion of the sacrificial layer adjacent the gate region, the sensing element forming the gate electrode;

forming a third insulating layer over the sensing element, a substantial part of the sacrificial layer and part of the passivation layer;

patterning and etching an opening through the third insulating layer to the sensing element;

filling the opening with conductive material to provide an electrically conductive path to the sensing element;

forming a fourth insulating layer over the third insulating layer and the electrically conductive path to the sensing element;

forming a shield layer on the fourth insulating layer;

forming a fifth insulating layer on the shield layer;

forming a conductive layer over a portion of the fifth insulating layer, the conductive layer providing a heater for the sensing element;

forming at least one hole through the conductive layer to the sacrificial layer; and removing the sacrificial layer so as to provide a cavity between the sensing element and second insulating layer.

15. A method for forming a semiconductor sensor FET device comprising the steps of:

providing a semiconductor substrate;

forming spaced-apart doped source and drain regions in the semiconductor substrate at a surface of the semiconductor substrate, the portion of semiconductor substrate between the source and drain regions defining a gate region;

forming a first insulating layer on the surface of the substrate;

patterning and etching first and second openings through the first insulating layer to the source and drain regions respectively;

filling the first and second openings with conductive material to provide electrically conductive paths to the source and drain regions;

forming a second insulating layer on the first insulating layer and electrically conductive paths;

forming a passivation layer on the second insulating layer;

forming a sacrificial layer on a portion of the passivation layer such that the sacrificial layer extends over the source, gate and drain regions;

forming a sensing element on a portion of the sacrificial layer adjacent the gate region, the sensing element forming the gate electrode;

forming a third insulating layer over the sensing element, a substantial part of the sacrificial layer and part of the passivation layer;

patterning and etching an opening through the third insulating layer to the sensing element;

filling the opening with conductive material to provide an electrically conductive path to the sensing element;

forming a fourth insulating layer over the third insulating layer and the electrically conductive path to the sensing element;

forming a shield layer on the fourth insulating layer;

forming a fifth insulating layer on the shield layer;

forming a conductive layer over a portion of the fifth insulating layer, the conductive layer providing a heater for the sensing element;

forming a passivation layer on the conductive layer;

forming at least one hole through the passivation layer to the sacrificial layer; and removing the sacrificial layer so as to provide a cavity between the sensing element and second insulating layer.

* * * * *